(12) United States Patent
Sarvazyan et al.

(10) Patent No.: US 6,468,231 B2
(45) Date of Patent: Oct. 22, 2002

(54) SELF-PALPATION DEVICE FOR EXAMINATION OF BREAST

(75) Inventors: Armen P. Sarvazyan, Lambertville; Vladimir Egorov, Plainsboro, both of NJ (US)

(73) Assignee: Artann Laboratories, Lambertville, NJ (US)

( * ) Notice: Subject to any disclaimer, the term of this patent is extended or adjusted under 35 U.S.C. 154(b) by 0 days.

(21) Appl. No.: 09/819,220

(22) Filed: Mar. 28, 2001

(65) Prior Publication Data

US 2001/0037074 A1 Nov. 1, 2001

Related U.S. Application Data

(60) Provisional application No. 60/193,985, filed on Mar. 31, 2000.

(51) Int. Cl.⁷ .......................... A61B 5/103; A61B 5/117
(52) U.S. Cl. ..................... 600/587; 600/595
(58) Field of Search .................. 600/550, 553, 600/587, 595; 73/81, 82; 33/511, 512

(56) References Cited

U.S. PATENT DOCUMENTS

| | | | |
|---|---|---|---|
| 4,250,894 A | 2/1981 | Frei et al. | 600/587 |
| 4,657,021 A | 4/1987 | Perry et al. | 600/300 |
| 4,793,354 A | 12/1988 | Wright et al. | 600/300 |
| 5,265,612 A | 11/1993 | Sarvazyan et al. | 600/471 |
| D348,618 S | 7/1994 | Leslie et al. | D10/64 |
| 5,524,636 A | 6/1996 | Sarvazyan et al. | 600/587 |
| 5,572,995 A | 11/1996 | Rohrberg | 600/300 |
| 5,640,325 A | 6/1997 | Banbrook et al. | 701/220 |
| 5,833,633 A | 11/1998 | Sarvazyan | 600/587 |
| 5,833,634 A | 11/1998 | Laird et al. | 600/587 |
| 5,860,934 A | 1/1999 | Sarvazyan | 600/587 |
| 5,916,180 A | 6/1999 | Cundari et al. | 600/587 |
| 5,989,199 A | 11/1999 | Cundari et al. | 600/587 |
| 6,091,981 A | 7/2000 | Cundari et al. | 600/407 |
| 6,162,191 A | 12/2000 | Foxlin | 600/595 |
| 6,179,790 B1 * | 1/2001 | Cundari et al. | 600/587 |
| 6,190,334 B1 | 2/2001 | Lasky et al. | 600/587 |
| 6,192,143 B1 | 2/2001 | Souluer | 328/128 |
| 6,351,549 B1 * | 2/2002 | Souluer | 382/131 |

OTHER PUBLICATIONS

C.R. Gentle, "Mammobarography: a possible method of mass breast screening," J. Biomed. Eng., vol. 10, pp.124–126, 1988.

* cited by examiner

Primary Examiner—Kevin Shaver
Assistant Examiner—Charles Marmor, II
(74) Attorney, Agent, or Firm—Mathews, Collins, Shepherd & McKay, P.A.

(57) ABSTRACT

A method and device in accordance with the present invention enable detecting changes in mechanical and structural properties of the breast tissue that are indicative of breast cancer development. In one embodiment of the invention, an array of force sensors based on PVDF piezopolymer film, data acquisition circuit, and a microprocessor are mounted in a hand held pad. Detection of nodules is achieved by pressing the sensing pad onto the breast, oscillating it over regions under investigation, and analyzing spectral and phase characteristics of the signal from the sensors in the array. The device is able to objectively detect presence of suspicious lesions in the breast and provide a warning signal.

14 Claims, 19 Drawing Sheets

SELF-PALPATION DEVICE FOR EXAMINATION OF BREAST

This application claims the benefit under 35 USC 119(e) of U.S. Provisional Application No. 60/193,985 filed Mar. 31, 2000.

This invention was made with government support under SBIR Grants No. 1 R43 CA65246-01 A1 and No. 2 R44 CA69175-03 awarded by the National Institutes of Health, National Cancer Institute. The government has certain rights in this invention.

Background of the Invention

1. Technical Field

The present invention relates to a method and apparatus for breast self-palpation and detecting changes of mechanical properties in the breast tissue that are indicative of breast cancer and other breast pathologies accompanied by changes in tissue viscoelasticity.

2. Description of the Related Art

Breast Cancer is a major source of cancer morbidity and mortality in women. Currently, the most widely used clinical diagnostic method is mammography. Efforts to reduce mortality via screening mammography have been successful with definite improvement in survival, particularly in women over 50 years old.

An alternative method—Breast Self-Examination (BSE) is the most common method of breast cancer detection. About two-thirds of cancers are detected by palpation. Such sensitivity of BSE is related to significant changes in mechanical properties of tissues in the course of breast cancer development. The BSE is widely advised and taught to women as a means of pre-clinical testing and contributes significantly to early cancer detection. A major fraction of breast cancer is first detected by women themselves, who bring the problem to the attention of their physicians. The usefulness of palpatory self-examination as a pre-clinical test is well proven by a wealth of data. The major drawback of this method is that only large size nodules are detectable by palpation. An average examiner, including women conducting breast self-examinations, does not reliably detect lesions until they approach 2 cm in diameter, which may represent a significantly advanced stage of cancer. Even a highly experienced examiner is able to detect a nodule only over 1 cm in diameter, which still may correspond to a considerably advanced cancer.

It is apparent, therefore, that further investigation into screening techniques with greater sensitivity is urgently warranted. Availability of an easy to use, hand-held device for a regular home testing will facilitate regular self-examinations conducted by women and lead to vast improvement in lowering the morbidity and mortality of breast cancer.

There have been many attempts to develop methods and devices for sensing the regions of hardening in tissues and thus, mimicking manual palpation aimed to detect breast cancer. Several authors have proposed various devices for breast palpation using different types of force sensors but all with limited success. For example, proposals by Gentle (Gentle C R, "Mammobarography: a possible method of mass breast screening", J. Biomed. Eng. 10, 124–126, 1988) was capable of detecting lumps of 6 mm in diameter in breast phantoms but was unable to obtain any quantitative data on lumps in a real breast. Many of the proposed BSE means were related to simple non-computerized mechanical systems enhancing sense of touch such as apparatuses described in U.S. Pat. No. 5,572,995, U.S. Pat. No. 4,657,021, U.S. Pat. No. 4,793,354, and U.S. Pat. No. D348,618 Various types of devices mimicking palpation to detect tumors using different types of force sensors have been suggested. For example, Frei et al., U.S. Pat. No. 4,250,894, have proposed an instrument for breast examination that uses a plurality of spaced piezoelectric strips which are pressed into the body being examined by a pressure member which applies a given periodic or steady stress to the tissue beneath the strips.

Another method and devices for breast self-examination is described in U.S. Pat. No. 5,833,634 and U.S. Pat. No. 5,989,199. The sensors used in those devices are based on a force sensor array manufactured by Tekscan Inc., Boston, Mass. The array consists of conductive rows and columns whose intersecting points form sensing locations. The rows and columns are separated by a material, which changes its electrical resistance under applied force, and thus each intersection becomes a force sensor.

SUMMARY OF THE INVENTION

The present invention, Self-Palpation Device (SPD), utilizes the same mechanical information as obtained by manual palpation conducted by a skilled physician but objectively and with higher sensitivity and accuracy. The proposed method and device provides detection of tissue heterogeneity and hard inclusions by measuring changes in the surface stress pattern using a force sensing array applied to the tissue in the oscillatory mode. Temporal and spatial changes of the spectral components and phase relationships of oscillatory signals from the sensors contain information on the mechanical properties and geometry of the internal structures of the breast.

The method and devices in accordance with the present invention enable the user to detect changes in the breast tissue that could be indicative of cancer development. The apparatus of the current invention uses sensors based on piezopolymer PVDF films and comprises mechanical arrangements allowing to increase PVDF signal while providing a good spatial resolution. PVDF film provides inexpensive means for measuring mechanical forces by converting them into an electrical signal. The apparatus also comprises a data acquisition circuit, and a microprocessor that are mounted in a hand held pad. Detection of nodules is achieved by analyzing the dynamic and spatial features of the measured signals obtained by pressing the probe to the breast and oscillating it over the area under investigation. The device is able to objectively detect the mechanical changes in a breast that could be an indication of cancer development.

The present invention provides indications on how elasticity differences in localized areas inside of tissue and respective changes in the spectral components as well as temporal and spatial derivatives of the oscillatory signals from the force sensors on the surface of the tissue are inter-related. The present invention also determines how the above relationship can be used for forming the basis for a method of detecting and quantifying tissue abnormalities.

A significant new feature of SPD is its learning ability needed for developing individually optimized diagnostic criteria. Learning algorithms implemented in the software of SPD make it possible to significantly increase the sensitivity of SPD by fine tuning the device to specific anatomical and physiologic features of a particular woman.

The learning ability of a home-use medical diagnostic system, such as the breast Self-Palpation Device of the present invention, is based on the fact that the data collected during an extended period of time provides means for defining much more precisely the "normal state" of a particular organ and thus, detecting meaningful deviations from the normal state with greater sensitivity.

Medical logic for diagnosis is typically based on the principle that healthy state of body is an objective notion and should be defined by "normal" intervals for vital parameters, which are the same for all people. For instance, if there are no palpable nodules in a breast, it is considered appropriate to qualify that breast "normal" from a mechanical point of view. At the same time, a particular, seemingly "normal", breast could have detectable mechanical changes resulting from a cancer development, but these changes are within the range of statistical variation of properties of the breast in general. Such meaningful changes can be detected only if one relates these changes to an individual baseline of a particular patient. The proposed self-palpation device of the present invention is based on a principle of medical diagnosis, by which the ranges of parameters that define the healthy state are determined individually.

Every human body is a complex dynamic system with a high level of self-adapting mechanisms. The term "normal range" for a parameter of an organism should be linked to its specific environment. In other words, while in one condition a particular range is normal, in another, the same range corresponds to an abnormality in the body.

The principle of individual normality can be described by using a formal model of a diagnostic process in general. A vector space A of "vital states" of an organ or entire organism can be considered. A single point (a vector a={a1, a2, . . . , ak} of the space) represents "an elementary temporal" state for a given organ or organism. The elementary state is defined by a set of vital parameters measured over a particular short period of time. Accordingly, the biological life of the investigated organism can be represented as a sequence of elementary states S=<s1, s2, . . . , sN> based on the sequence of the periods T={1,2, . . . , N}. Every element from the sequence is a point in A, and the sequence S can be interpreted as a trajectory of "elementary" transformations Ts(i)=s(i+1). The main idea to introduce "individual standard" for "normal" and "abnormal" states is based on the well known fact that if a clinician looks at a single element s(i) from S, he/she often cannot estimate the normality of the state, but if he/she can observe the entire sequence S the estimation of s(i) is not a hard problem in the most of cases.

The sequence S can be presented by an average state s*(S). Variance v(s*) of the average is a simplest measure of uncertainties of how well s* represents S. If v(s*) is small enough the representation gives a good approximation for S. This state will be referred to as "stable temporally and individually" because of its stability during a long period of life time. If the variance for every vital parameters is small during period T and the average value for each of them belongs to "objective" intervals of norms the s*(S) as will be referred to as "normal" for a given patient for the period of time T. Otherwise, the state of S will be referred to as "abnormal".

In the extended sequence of elementary states S'={S, s(N+1)}, the elementary state s(N+1) is called "alarm-state" if the state of S is normal while the state of S' is abnormal.

The principle of "individual normality" of the breast proposed in the present invention is based on a predefined choice of concrete values for several parameters (such as N, thresholds on variances for all vital parameters, etc.). The list of parameters which can be considered "relevant" and can be used as state characteristics need to be predefined.

In general, there are many approaches to represent a set by its members. For example, one can use a simple average representation. Other approaches, such as median representatives, can also be used.

With the foregoing and other objects, advantages and features of the invention that will become hereinafter apparent, the nature of the invention may be more clearly understood by referencing to the following detailed description of the invention, the appended claims and the several views illustrated in the drawings.

DETAILED DESCRIPTION OF THE INVENTION

Figure 1A:
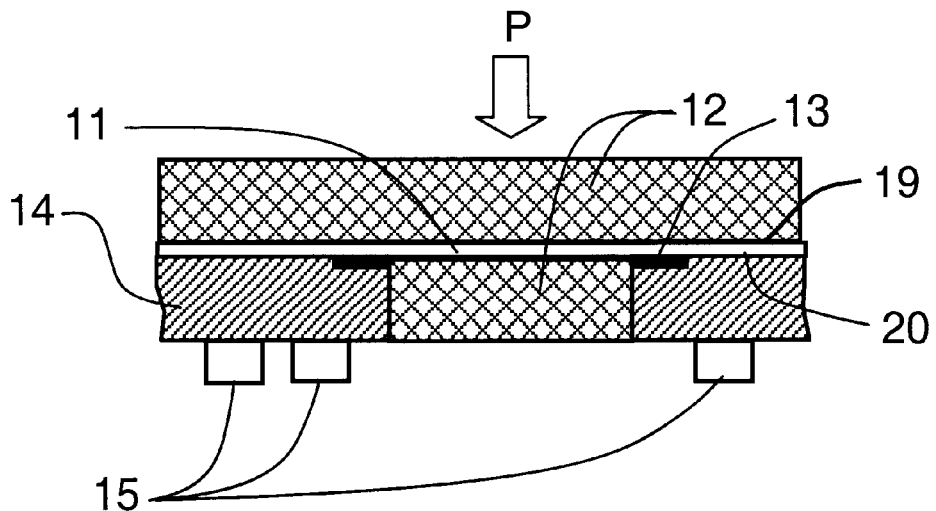
FIG. 1A is a cross-section of PVDF based force sensor.
Figure 1B:
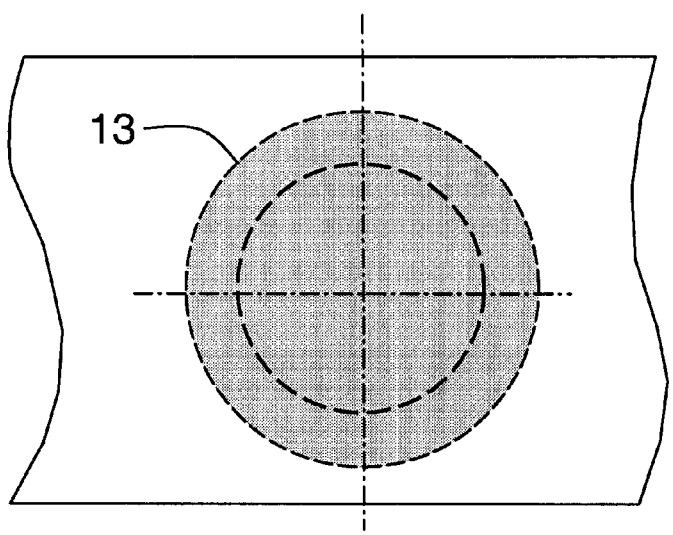
FIG. 1B is a top view of PVDF based force sensor shown in FIG. 1A.

Referring now to the drawings, like elements are designated by like numerals, FIGS. 1A, 1B show an arrangement to mechanically amplify a PVDF sensor signal by converting a small force into a high tangential tension. PVDF based force sensor 10 comprises sensing elements 11 made of PVDF film and printed circuit board (PCB) 14 with a round opening. Electronic components 15 are mounted at the bottom of PCB 14. PVDF sensing element 11 has metallization on both surfaces in order to collect a charge. Top metallization layer 19 covers the entire surface and it is connected to the common point of electrical circuit. Bottom metallization layer 20 is a circle slightly larger in diameter than the opening in PCB (see FIG. 1B). PCB 14 has a round contact 13 to get collected charge to electronic components 15. Top metallization layer 19 of PVDF film 11 also acts as an electric shield to eliminate noise pick up.

Figure 2:
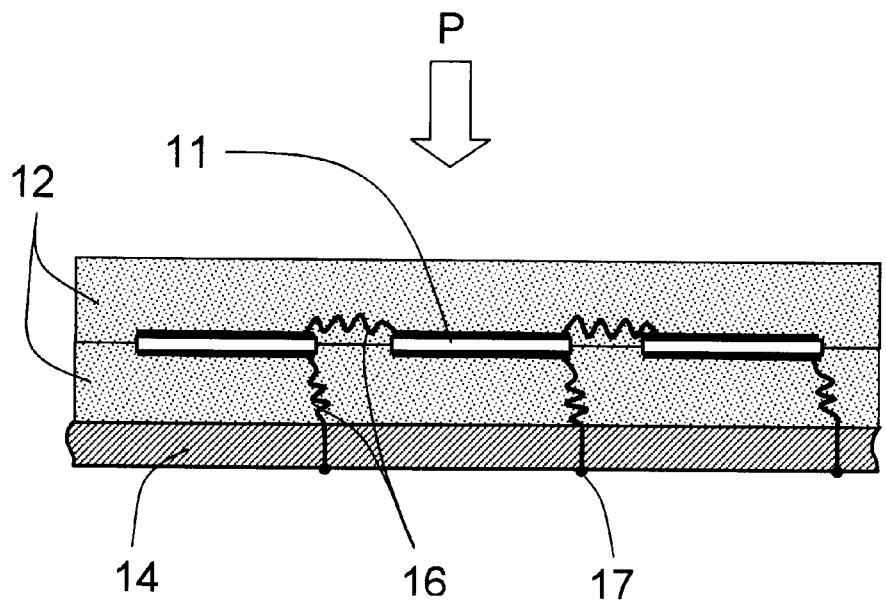
FIG. 2 is a cross-section of another PVDF based force sensor.
Figure 3:
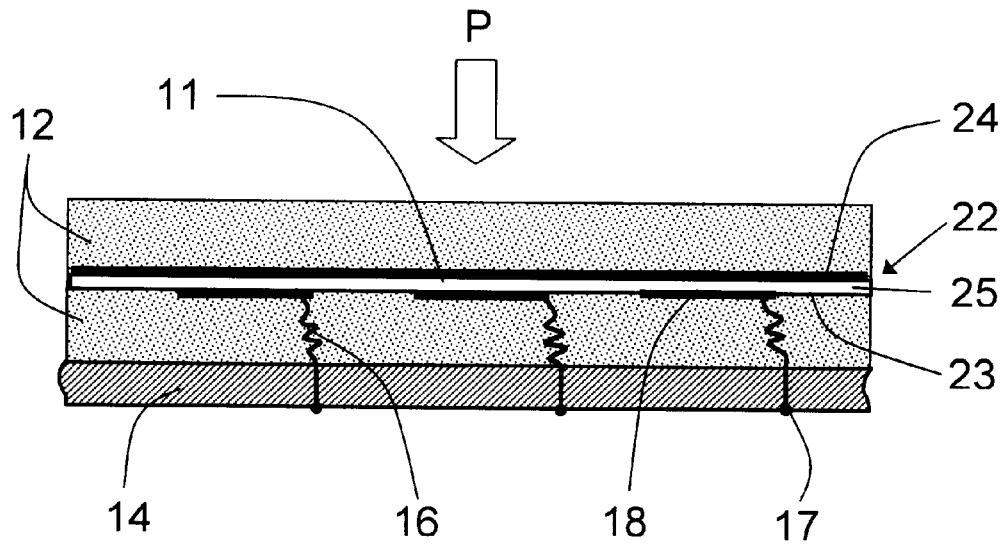
FIG. 3 is a cross-section of yet another embodiment of PVDF based force sensor.

FIGS. 2 and 3 show other embodiments of PVDF based force sensor arrays with PVDF sensing elements 11 embedded into elastic material 12 covering the surface of PCB 14. For example, elastic material 12 can be a soft rubber. When a force is applied to PVDF sensor 11 it results in bending, stretching and tangential tension in the PVDF material and generating electrical charge on the electrodes of the sensors. The embodiment shown in FIG. 2 comprises individual PVDF sensors 11 connected by thin elastic wiring 16 with contact points 17 of PCB 14. The electrodes on the other side of the PVDF sensors, opposite to PCB, are interconnected and grounded. PVDF sensors 22 of the embodiment shown in FIG. 3 are formed by electrodes 18 on surface 23 of a single PVDF sheet 25. Opposite surface 24 of PVDF sheet is metallized and grounded. This ground electrode layer acts also as an electric shield to eliminate noise pick up.

Figure 4:
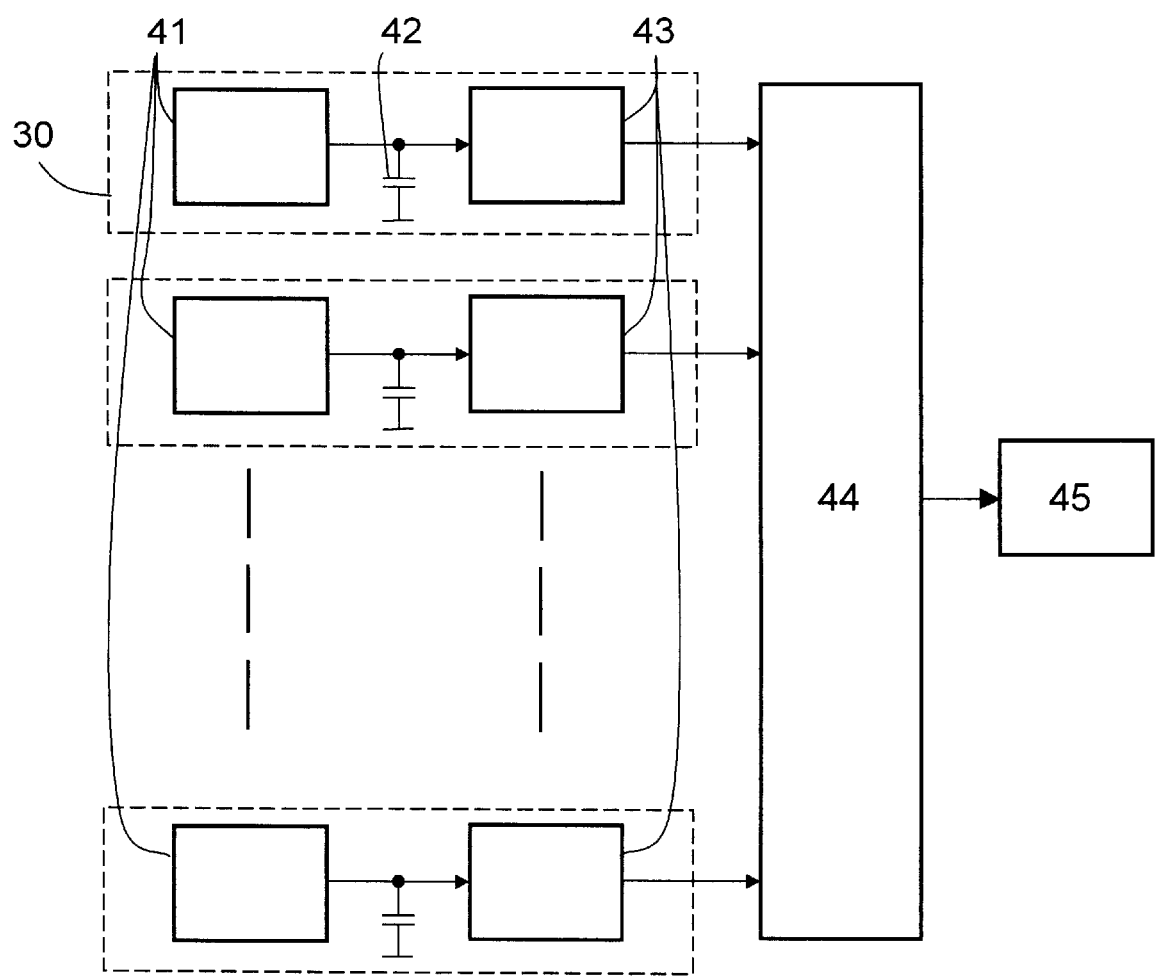
FIG. 4 shows the arrangements to convert PVDF sensor signals to a digital form.

FIG. 4 shows an arrangement for converting PVDF sensor signals into a digital form. Multiple cells 30 are connected to a multiplexer 44. Each cell 30 has PVDF sensor 41, external capacitor 42 and high input impedance amplifier 43. External capacitor 42 increases the time constant. Output of multiplexer 44 goes to analog-to-digital converter 45 to be converted into digital form and fed to a computer.

Figure 5:
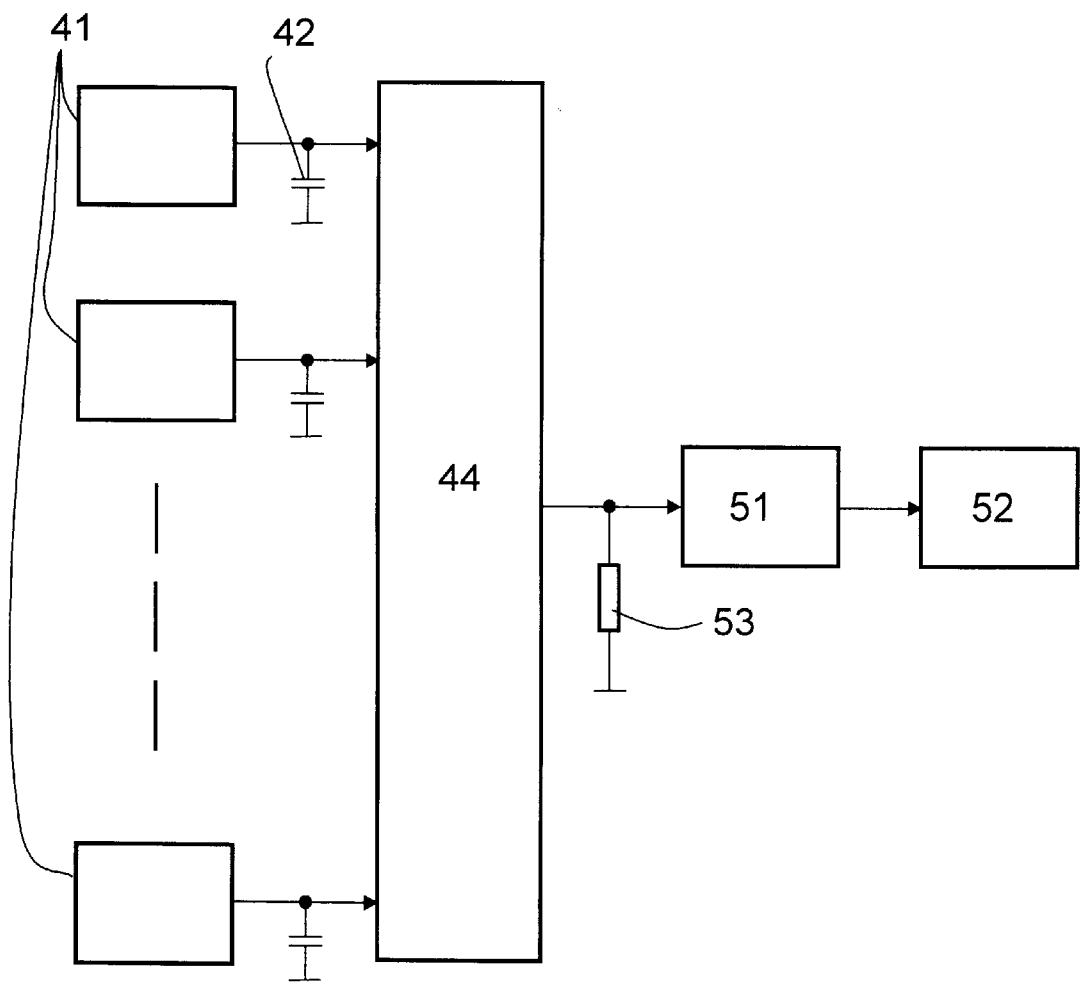
FIG. 5 shows a different arrangement to convert PVDF sensor signals to a digital form.

FIG. 5 shows an alternative arrangement 50 of converting PVDF sensor signals into a digital form. Arrangement 50 includes PVDF sensors 41, external capacitors 42, and multiplexer 44, bleeding resistor 53, high input impedance amplifier 51 and analog-to-digital converter 52. The use of one amplifier on the output of multiplexer 44 instead of individual amplifiers for each sensor substantially reduces the cost and power consumption.

Figure 6:
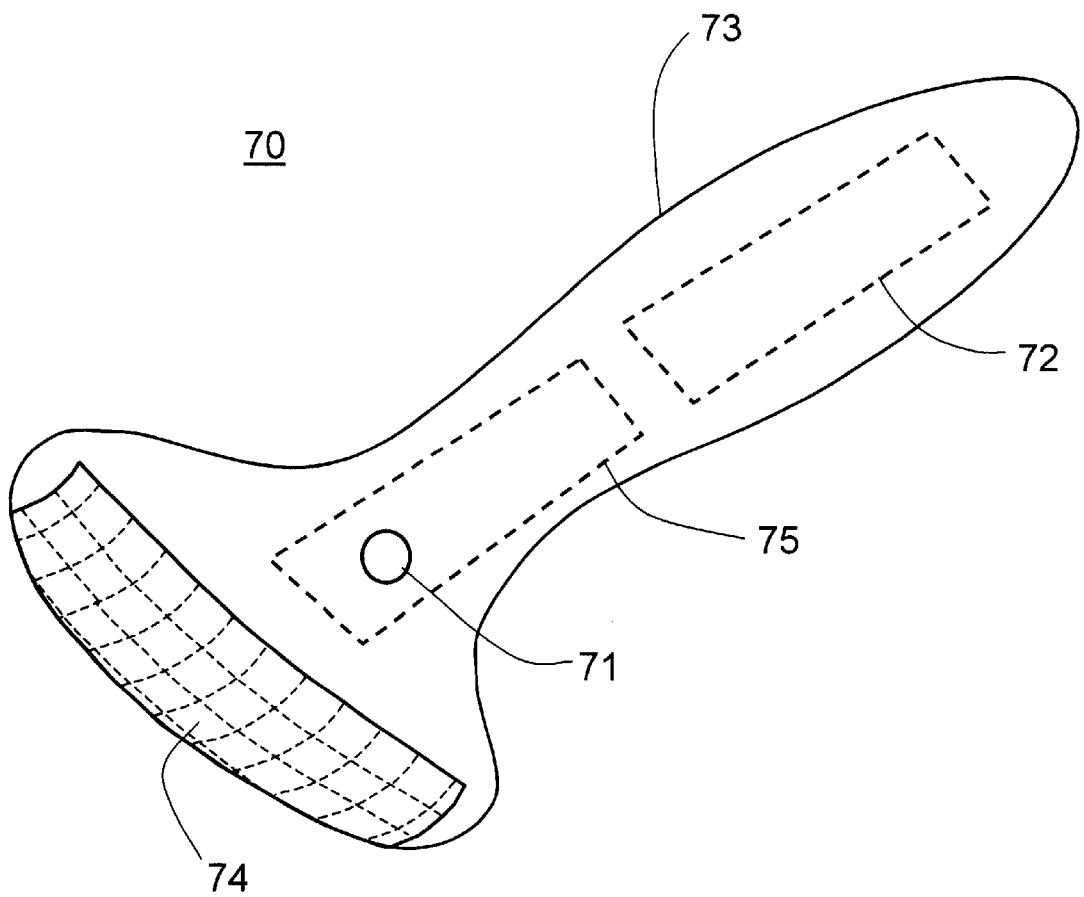
FIG. 6 is a general view of an embodiment of a self-palpation device.
Figure 7:
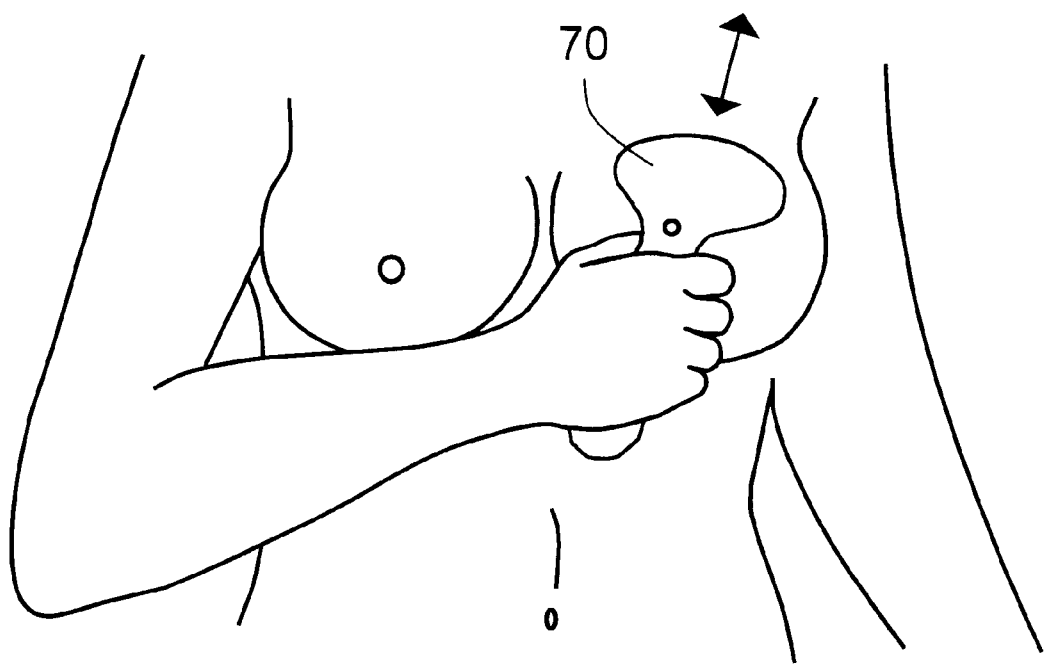
FIG. 7 represents the self-palpation device shown in FIG. 6 in use.

Referring to FIG. 6, self-palpation device 70 includes a plurality of force sensing transducers 74. Force sensing transducers 74 can be similar to arrays shown in FIGS. 1, 2 and FIG. 3. Force sensing transducers 74 generate signals, which vary with the force applied by the contact with the breast tissue and dynamic properties of the force sensors. Device 70 also includes electronic board 75, housing 73, electric power supply 72, such as a battery, and signal light 71. FIG. 7 represents self-palpation device 70 of FIG. 6 in use. During operation of self-palpation device 70, it is pressed gently against the breast and then is oscillated over the breast.

Figure 8:
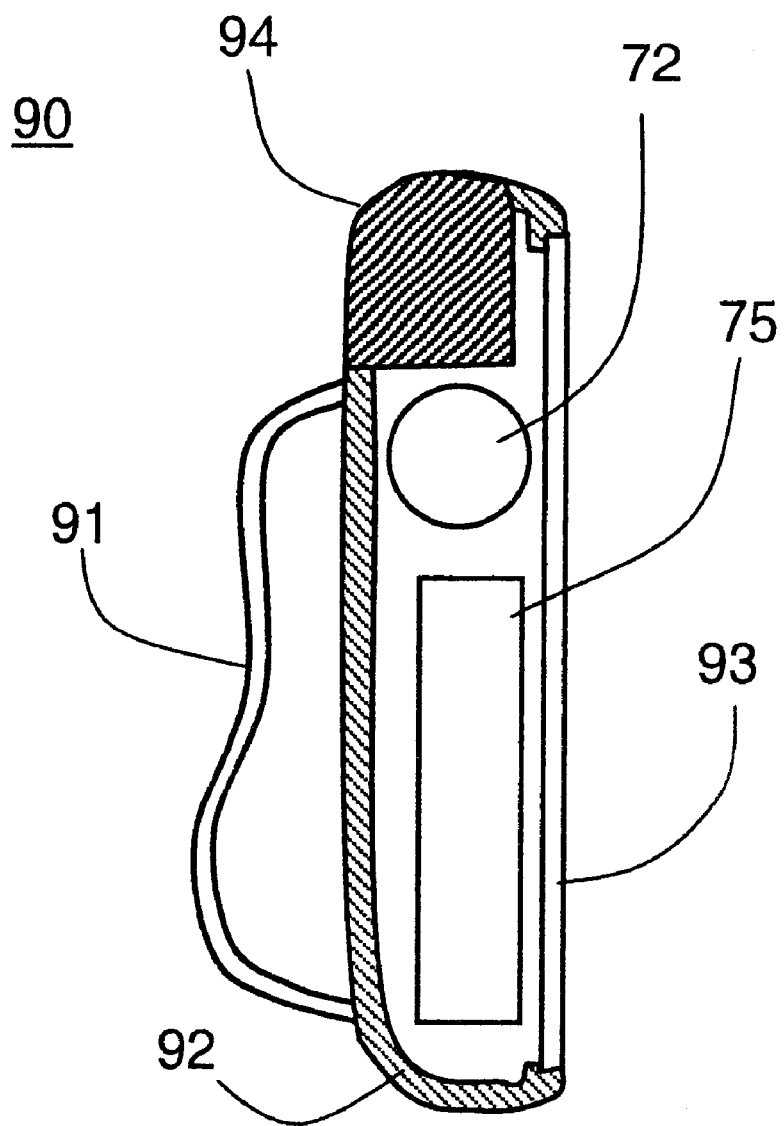
FIG. 8 is across-section side view of another embodiment of self-palpation device.
Figure 9:
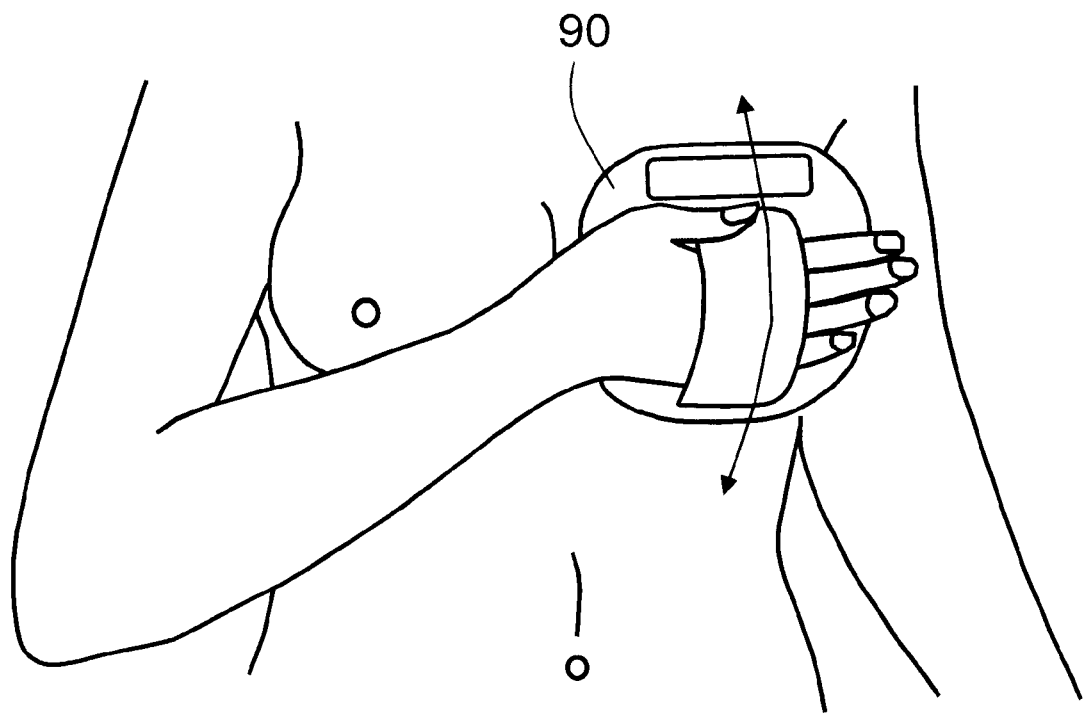
FIG. 9 represents the self-palpation device shown in FIG. 8 in use.

FIG. 8, shows an alternative self-palpation device 90 that comprises a force sensor array 93 composed of sensors shown in FIGS. 1–3. Device 90 also includes electronic board 75, housing 92, electric power supply 72, display 94, and belt fastener 91. FIG. 9 represents the self-palpation device 90 of FIG. 8 in use. During operation of self-palpation device 90, it is pressed gently against the breast and then is oscillated over the breast.

Figure 10:
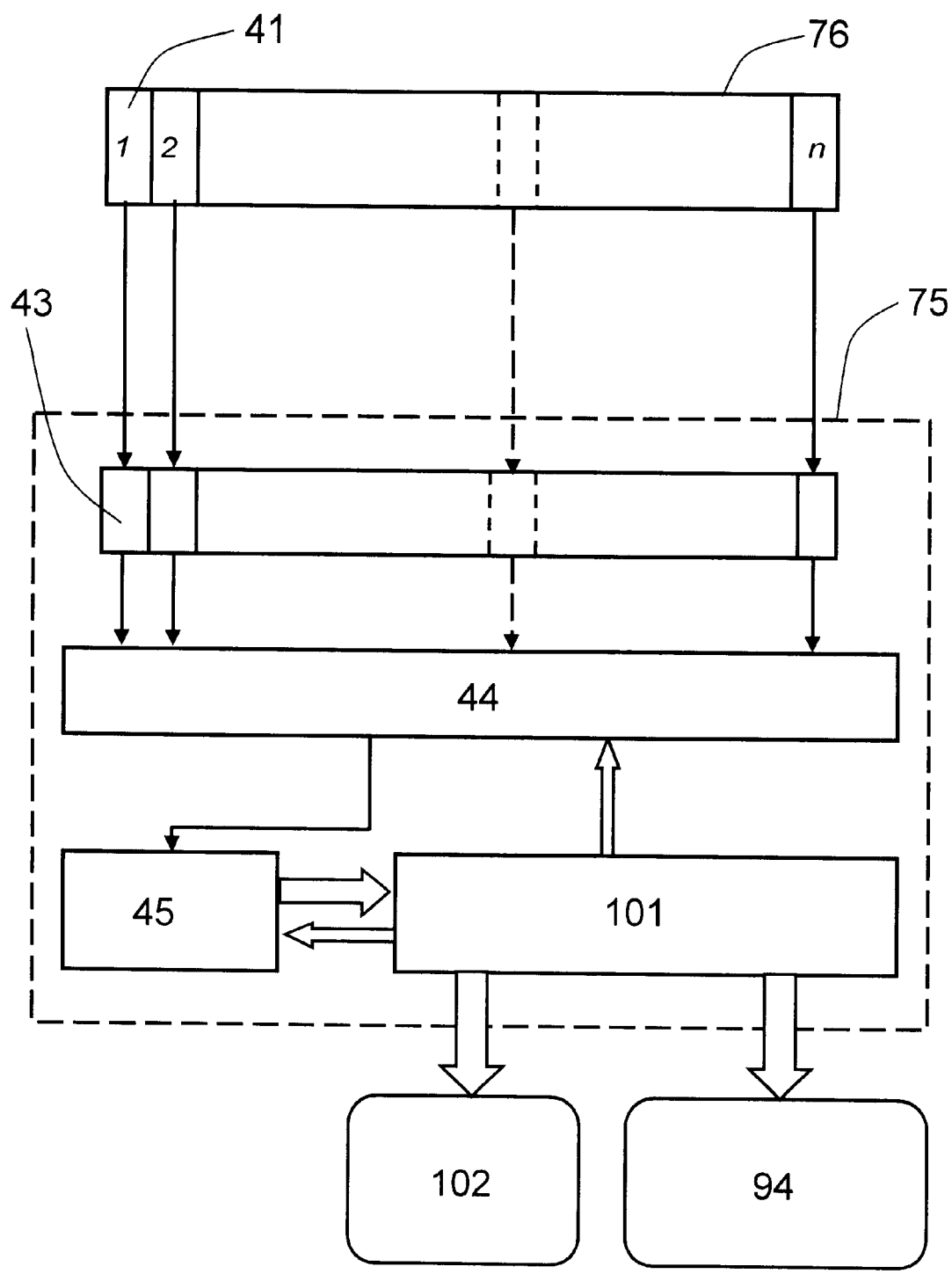
FIG. 10 is a schematic diagram of an electronic unit for acquisition, processing and displaying mechanical imaging data from the self-palpation devices shown in FIG. 6 and FIG. 8.

FIG. 10 is a schematic diagram of an electronic unit for providing acquisition, processing and displaying of mechanical imaging data from the self-palpation devices shown in FIG. 6 and FIG. 8. FIG. 10 illustrates a schematic diagram of a preferred embodiment of the electronic unit 75 which is coupled to self-palpation device 70 or self-palpation device 90 (not shown). A plurality of PVDF sensor elements 41 form force sensor assembly 76 of the device. A force sensing circuit is formed of a plurality of amplifiers 43 to amplify respective signals generated by force PVDF sensor elements 41 of force sensor assembly 76. The amplified signals from amplifiers 43 are applied to the multiplexer 44. Multiplexed signals are converted into digital signals by analog-to-digital converter 45 and fed to a processor 101. Display device 94 is connected to the processor 101, thereby displaying the breast examination process and the results of the examination. Processor 101 communicates with analog-to-digital converter 45 and multiplexer 44 for sending data and control signals. Storage device 102 having PC connector port can store examination data and transfer it to a computer.

Figure 11:
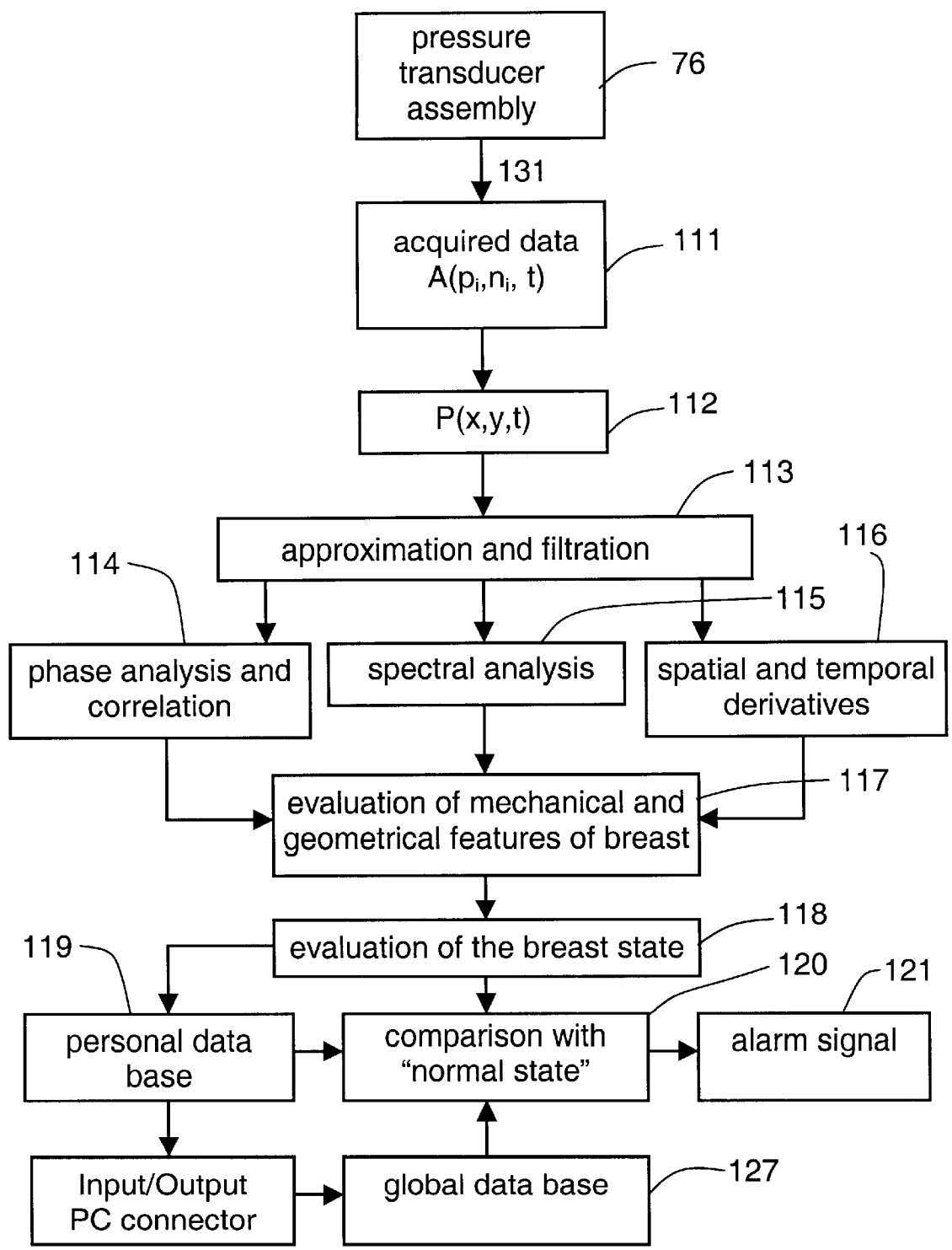
FIG. 11 shows a flow chart representative of an algorithm for obtaining diagnostic information on the state of a breast from the data obtained by the force sensor array.

FIG. 11 shows a flow chart representative of an algorithm for determining diagnostic information from palpation data. Force data 131 from force sensor assembly 76 are acquired in real-time. Analog signals representing the force measured from all the force transducers of the force sensor assembly 76 at time t form force data flow 131. In box 111, force data flow 131 are combined over time into acquired data represented by $A(p_i, n_i, t)$. Using force calibration data, the acquired data are combined over a period of time to form force data file $P(x, y, t)$ in box 112. In box 113, data file $P(x, y, t)$ is processed by one of the known approximation and filtration methods, as described for example by J.-L. Stark, F. Murtagh and A. Bijaouiet, *Image Processing and Data Analysis*, Cambridge University Press (1998). In boxes 114, 115, and 116 the data is further analyzed and phase correlations, spectral composition of the signals, and spatial and temporal derivatives of the signals are evaluated and forwarded to box 117 for evaluating mechanical and geometrical features of the breast. Based on mechanical and geometrical parameters the state of the examined breast is estimated in box 118 and compared to the "normal state" 120 using information from global data base from box 127. When the deviation of the state of the breast from the "normal state" exceeds a predetermined level, the device produces an alarm signal in box 121. Information on every particular examination is collected in the personal data base in box 119. After accumulating sufficient data on the states of the particular breast the system generates an adjusted personalized definition of the "normal state" and subsequently, the detection of the anomalous development significantly improves.

Figure 12A:
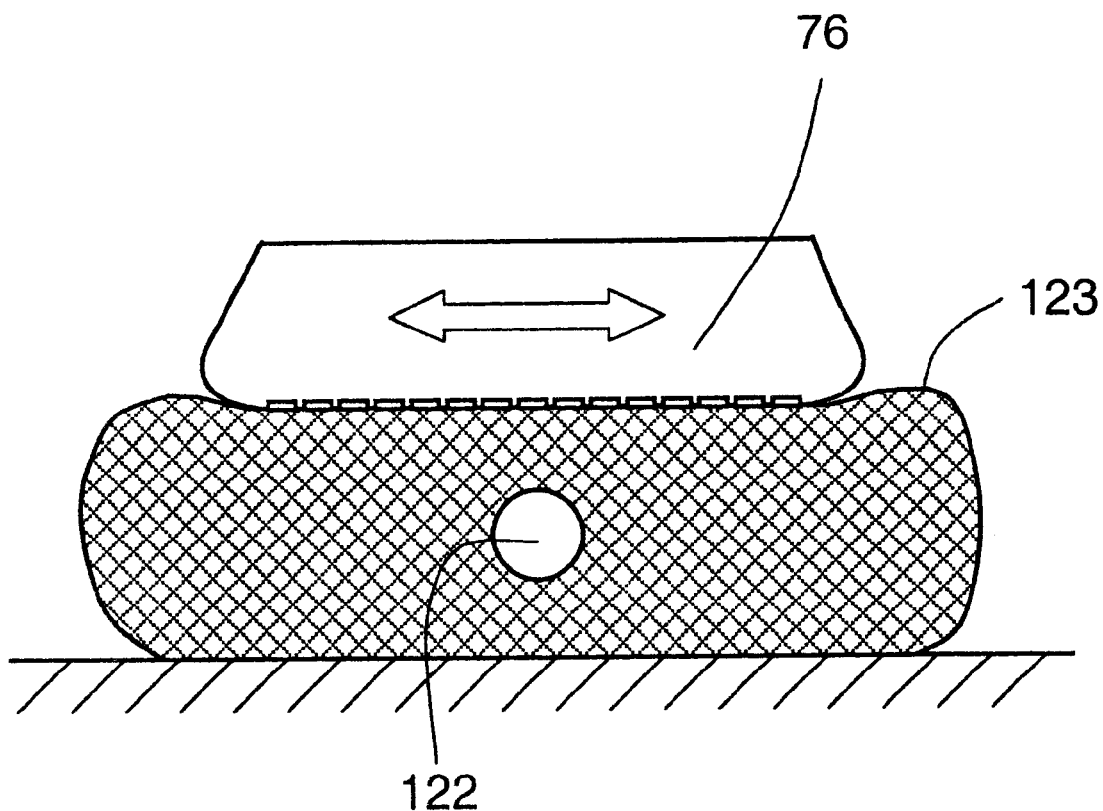
FIG. 12A shows a sectional view of the force-sensor array pressed against a tissue phantom with hard inclusion.

FIG. 12A is a sectional view showing the force sensor assembly 76 pressed against a tissue phantom 123 with a hard inclusion 122. Oscillating the probe over the phantom enables detecting the hidden nodules and evaluating their parameters: the diameter, hardness and depth.

Figure 12B:
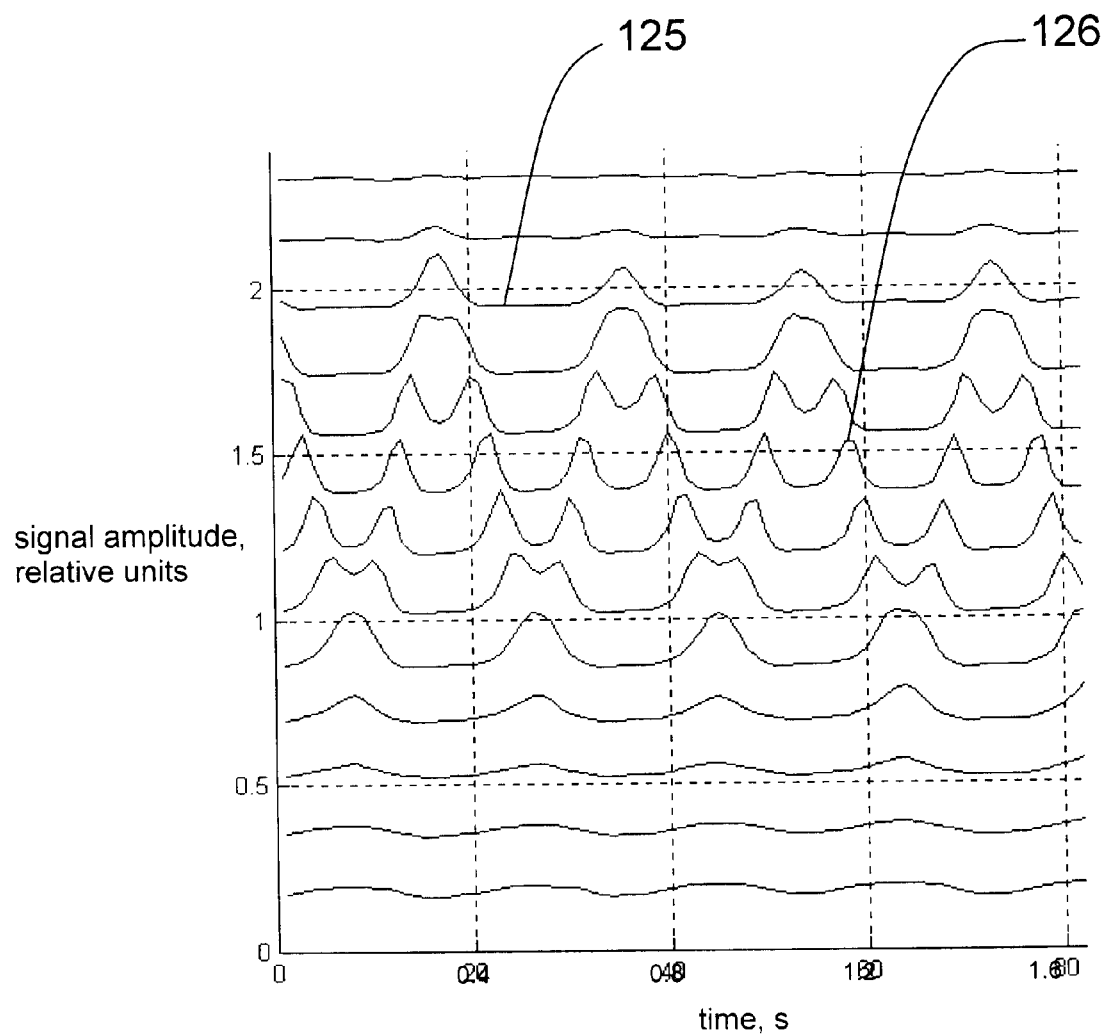
FIG. 12B is a graphical representation of a time dependence of signals from force sensors in one row of the array in the process of the experiment shown in FIG. 12A.

FIG. 12B is a graphical representation of time dependence of signals from the force sensors in one row of the array in the process of the experiment shown in FIG. 12A. The difference in the time profiles of signals from the sensors located at different positions with regard to the nodule, as seen in records 125 and 126, allows detecting and evaluating parameters of nodules.

Figure 12C:
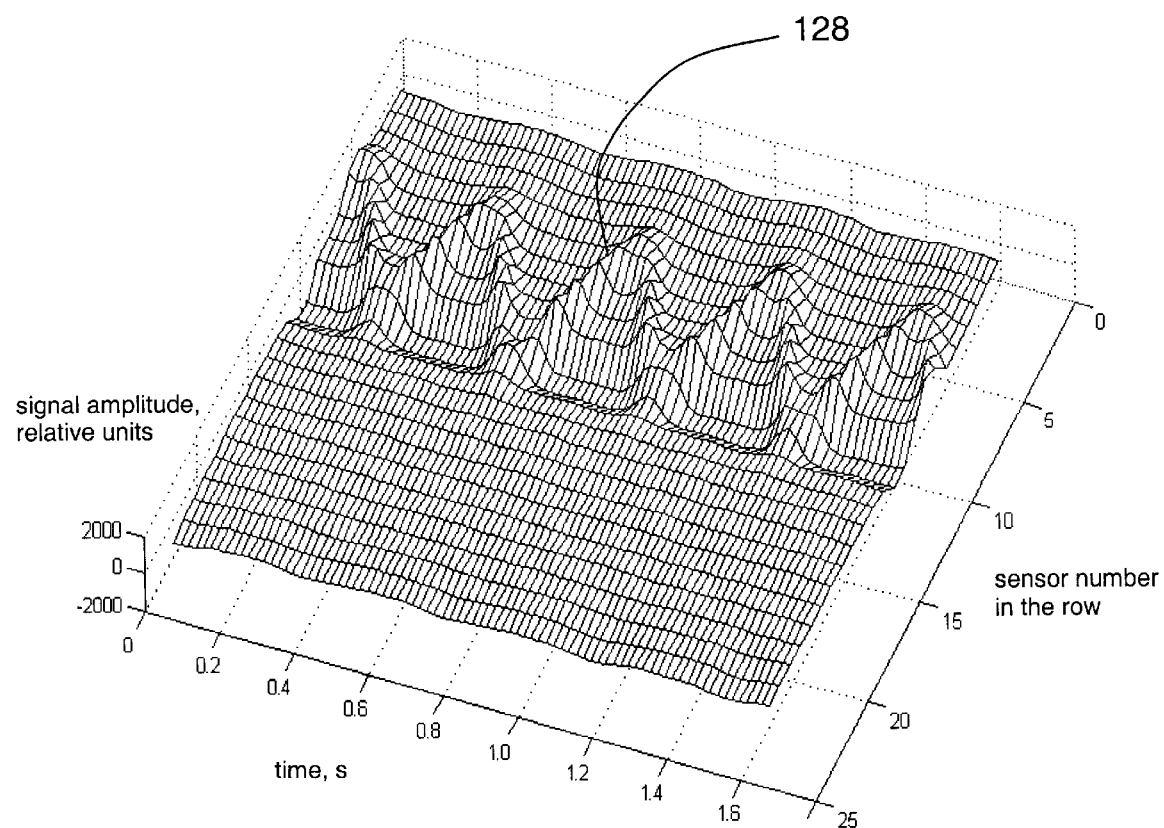
FIG. 12C is a graphical representation of a time dependence of signals from force sensors from the entire array in the process of the experiment shown in FIG. 12A.

FIG. 12C is a different graphical representation of the data presented in FIG. 12B showing clearly the trace 128 formed by the inclusion on the time dependence of the force pattern. FIGS. 12B and 12C illustrate sensitivity of temporal and spatial derivatives of the force sensor array signals to the presence of mechanical heterogeneity such as a hard nodule in the examined tissue.

Figure 13:
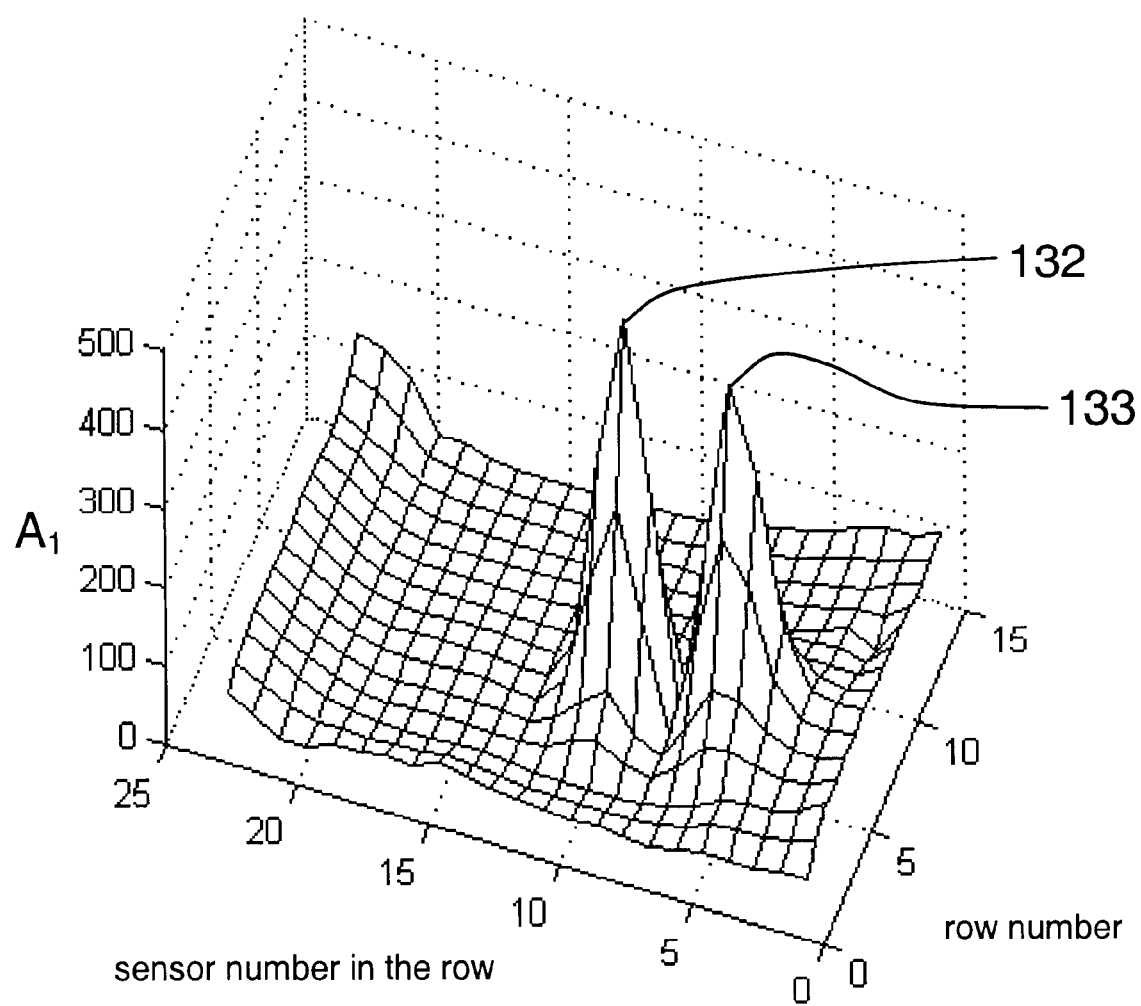
FIG. 13 shows spatial distribution of the amplitude of the first harmonic of the oscillatory signals shown in FIG. 12C.

FIG. 13 is a graphical representation of amplitude of the first harmonic $A_1$ for the data of FIG. 12C. Presence of the nodule results in the appearance of two distinctly expressed peaks 132 and 133.

Figure 14:
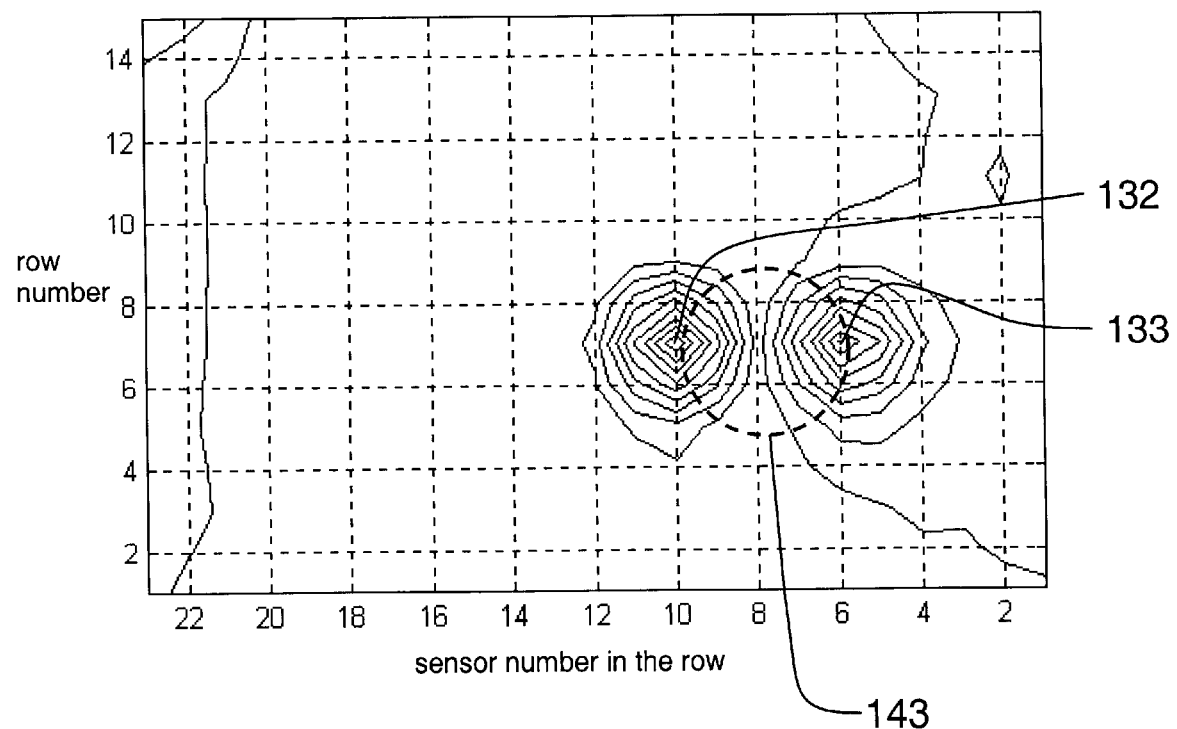
FIG. 14 is a topographic representation of the data shown in FIG. 13.

FIG. 14 is a topographic representation of amplitude of the first harmonic obtained from the same data as in FIG. 13. The location of the nodule is shown by dotted circle 143.

Figure 15:
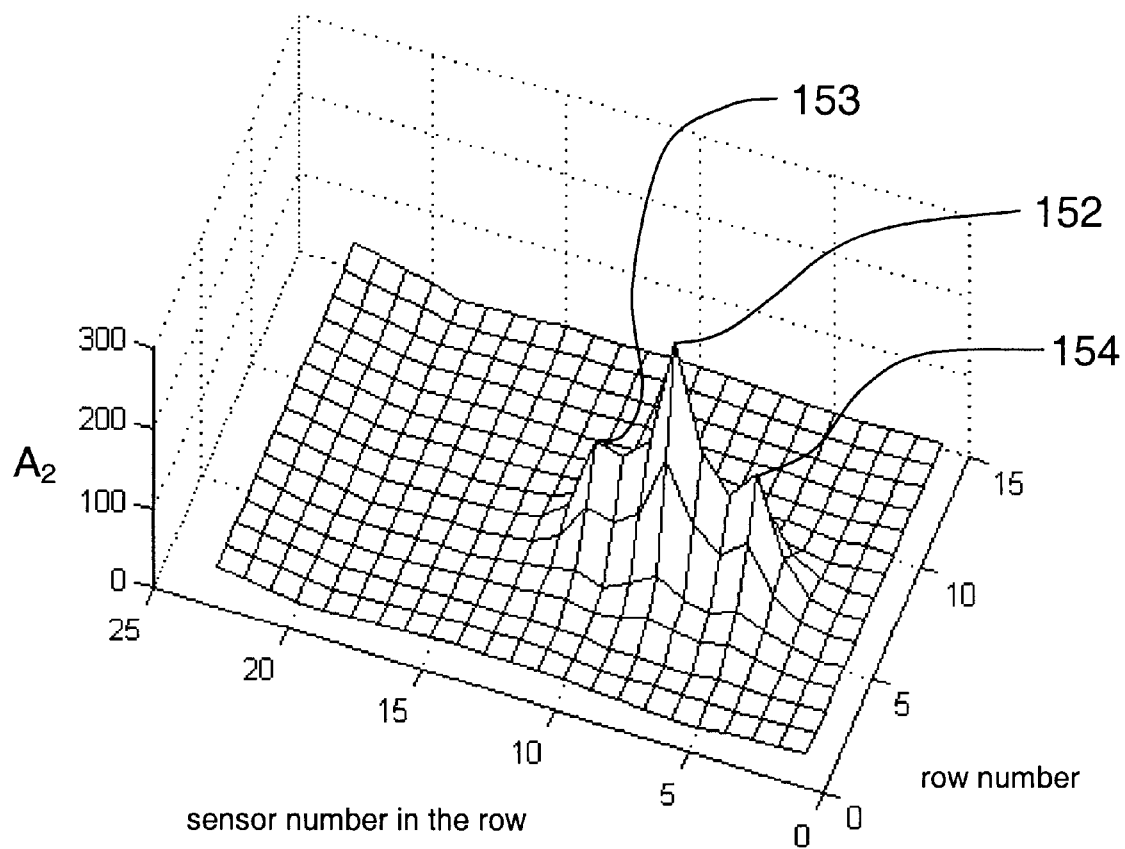
FIG. 15 shows spatial distribution of the amplitude of the second harmonic of the oscillatory signals shown in FIG. 12C.

FIG. 15 shows a spatial distribution of the amplitude of the second harmonic $A_2$ of the oscillatory signals shown in FIG. 12C. Presence of the nodule is clearly revealed by maximum 152 of the second harmonic with two characteristic shoulders 153 and 154 at the position of the first harmonic maxima shown in FIG. 13.

Figure 16:
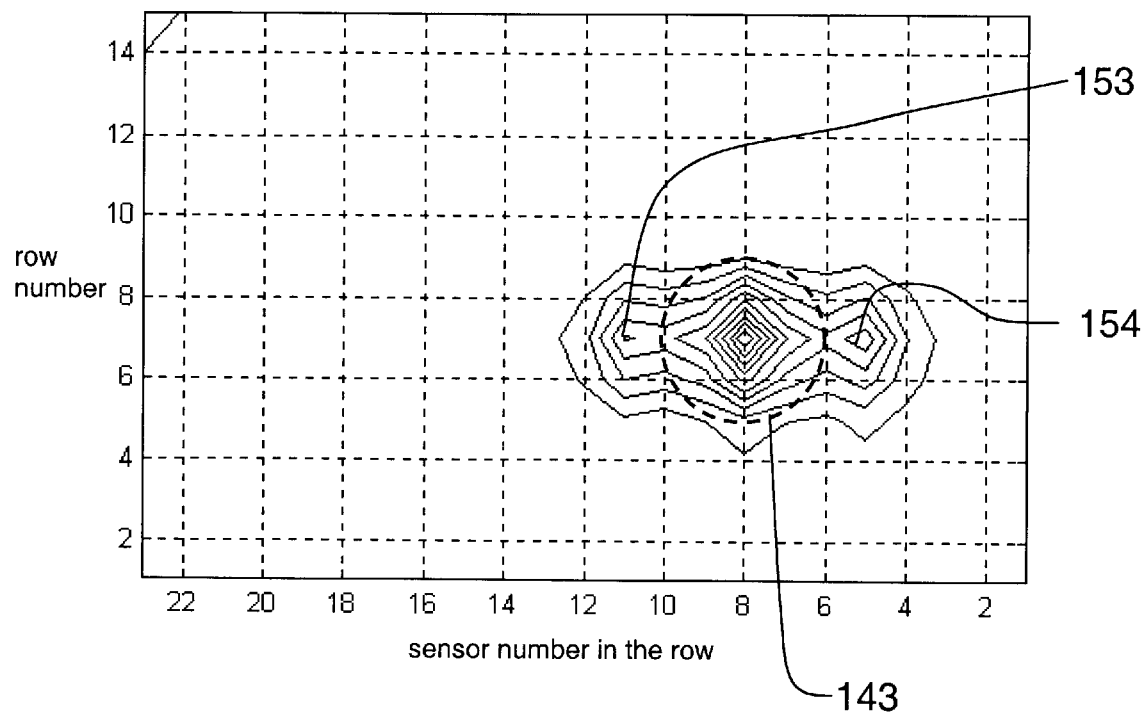
FIG. 16 is a topographic representation of the data shown in FIG. 15.

FIG. 16 is a topographic representation of the data shown in FIG. 15. The nodule located in the region shown by the circle 143 is detected without any ambiguity from the pattern of the second harmonic distribution with maximum 152 and shoulders 153 and 154.

Figure 17:
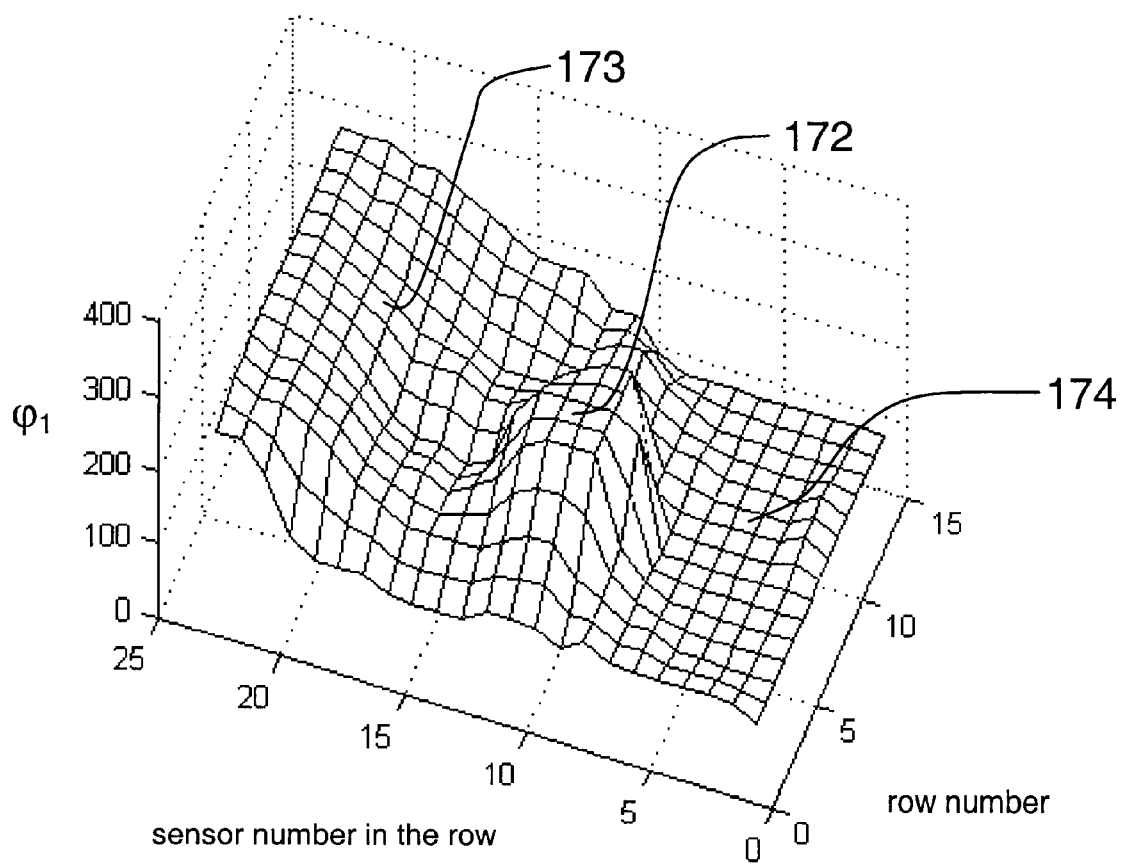
FIG. 17 shows spatial distribution of the phase shift of the first harmonic of the oscillatory signals shown in FIG. 12C.

FIG. 17 is a graphical representation of the phase shift of the first harmonic for force signals calculated from the data of FIG. 12C. In the vicinity of the location of the nodule the phase of the oscillatory signal experiences significant changes. The phase of the signal changes up to 180° from region 173 to region 174 having the steepest slope at the location of the nodule, as it is seem more clearly in FIG. 18.

Figure 18:
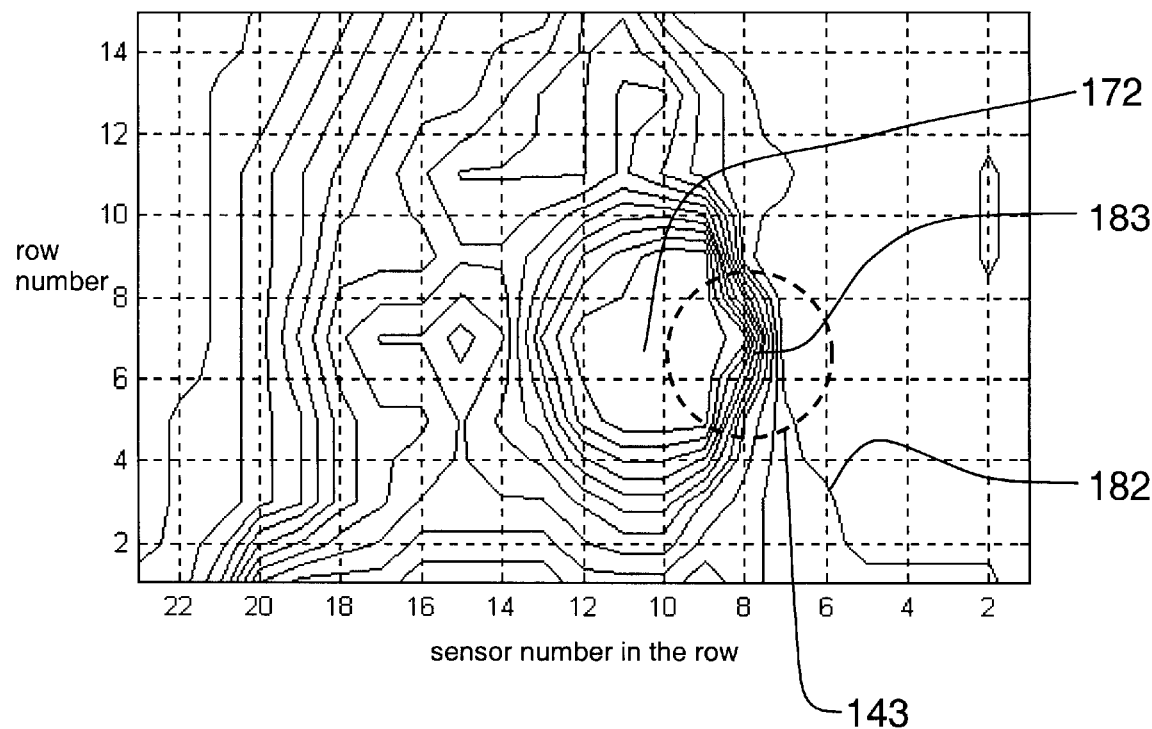
FIG. 18 is a topographic representation of data shown in FIG. 17.

FIG. 18 is a topographic representation of a phase shift of the first harmonic showing the same data as FIG. 17. Phase inversion is observed while moving along the row of the sensors from region 172 to region 182 located on two opposite sides of the nodule located at the region denoted by the circle 143. The phase inflection point 183 corresponds to the exact location of the nodule.

FIGS. 12–18 clearly illustrate the possibility to use dynamic features of the oscillatory signals from the force sensor array to detect hard inclusions imbedded in the soft tissue.

Although certain presently preferred embodiments of the present invention have been specifically described herein, it will be apparent to those skilled in the art to which the invention pertains that variations and modifications of the various embodiments shown and described herein may be made without departing from the spirit and scope of the invention.

What is claimed is:

1. A method of detecting changes in mechanical and structural properties of breast tissue that are indicative of breast cancer development, said method comprising the steps of:
   causing an oscillatory deformation of a breast tissue portion by a force sensor array pressed against that tissue portion;
   detecting an oscillatory signal from the sensors of the force sensor array;
   repeating said oscillatory deformation over a plurality of breast tissue portions;
   detecting an oscillatory signal from the sensors of the force sensor array;
   analyzing the signals from sensors in the array;
   evaluating type and degree of mechanical heterogeneity of the breast tissue;
   evaluating deviation of the type and degree of mechanical heterogeneity of the breast from a normal range of mechanical heterogeneity of the breast; and
   producing a warning signal if said deviation of mechanical heterogeneity of the breast exceeds a predetermined threshold.

2. The method of claim 1 wherein said normal range of mechanical heterogeneity of the breast is defined using a global database on mechanical properties and structure of the breast.

3. The method of claim 1 wherein said normal range of mechanical heterogeneity of the breast is defined individually, using a personal database on mechanical properties and on structure of the breast accumulated during previous examinations.

4. The method of claim 1 wherein said step of analyzing the signals from sensors in the array includes analyzing spectral and phase characteristics of the signals.

5. The method of claim 4 wherein said spectral and phase characteristics of the signals include the amplitude of the first harmonic, the amplitude of the second harmonic and phase shifts of these harmonics.

6. The method of claim 1 wherein said analyzing the signals from sensors in the array includes analyzing spatial and temporal derivatives of the signals from sensors in the array.

7. A hand-held device for implementing the method of the claim 1 wherein said force sensor array comprises: an array of piezopolymer based force sensors formed of a piezopolymer film activated by flexural and extensional modes of deformation of the piezopolymer film;
   data acquisition means for receiving said oscillatory signals;
   a microprocessor used for said step of analyzing the signals and said steps of evaluating type and degree of mechanical heterogeneity of the breast and evaluating deviation of the type and degree of mechanical heterogeneity of the breast from the normal range; and
   a means for producing the warning signal.

8. A system for detecting changes in mechanical and structural properties of breast tissue that are indicative of breast cancer development, said system comprising:
   means for causing an oscillatory deformation of a breast tissue portion by a force sensor array pressed against that tissue portion;
   means for detecting an oscillatory signal from the sensors of the force sensor array;
   means for repeating said oscillatory deformation over a plurality of breast tissue portions;
   means for detecting an oscillatory signal from the sensors of the force sensor array;
   means for analyzing the signals from sensors in the array;
   means for evaluating type and degree of mechanical heterogeneity of the breast tissue;
   means for evaluating deviation of the type and degree of mechanical heterogeneity of the breast from a normal range of mechanical heterogeneity of the breast; and
   means for producing a warning signal if said deviation of mechanical heterogeneity of the breast exceeds a predetermined threshold.

9. The system of claim 8 wherein said normal range of mechanical heterogeneity of the breast is defined using a global database on mechanical properties and structure of the breast.

10. The system of claim 8 wherein said normal range of mechanical heterogeneity of the breast is defined individually, using a personal database on mechanical properties and on structure of the breast accumulated during previous examinations.

11. The system of claim 8 wherein said means for analyzing the signals from sensors in the array includes means analyzing spectral and phase characteristics of the signals.

12. The system of claim 11 wherein said spectral and phase characteristics of the signals include amplitude of a first harmonic, amplitude of a second harmonic and phase shifts of said harmonics.

13. The system of claim 8 wherein said means for analyzing the signals from sensors in the array includes means for analyzing spatial and temporal derivatives of the signals from sensors in the array.

14. A hand held device for detecting changes in mechanical and structural properties of breast tissue that are indicative of breast cancer development comprising:

an array of piezopolymer based force sensors formed of a piezopolymer film activated by flexural and extensional modes of deformation of the piezopolymer film as said array is pressed against the breast tissue;

data acquisition means for receiving signals from said array;

means for analyzing said data to determine type and degree of mechanical heterogeneity of the breast;

means for evaluating deviation of the type and degree of mechanical heterogeneity of the breast from a normal range of mechanical heterogeneity of the breast; and means for producing an alarm signal if said deviation of mechanical heterogeneity of the breast exceeds a predetermined threshold.

* * * * *